(12) United States Patent
Kardeis et al.

(10) Patent No.: US 7,316,424 B2
(45) Date of Patent: Jan. 8, 2008

(54) FAST-FIT COUPLING FOR CONNECTING APPLIANCES FORMING PART OF A MEDICAL OR SURGICAL HANDPIECE SYSTEM TO A SUPPLY HOSE

(75) Inventors: Richard Kardeis, Bürmoos (AT); Wolfgang Wendtner, Lamprechtshausen (AT)

(73) Assignee: W&H Dentalwerk Burmoos GmbH, Burmoos (AT)

( * ) Notice: Subject to any disclaimer, the term of this patent is extended or adjusted under 35 U.S.C. 154(b) by 0 days.

(21) Appl. No.: 10/735,317

(22) Filed: Dec. 11, 2003

(65) Prior Publication Data

US 2004/0124631 A1 Jul. 1, 2004

(30) Foreign Application Priority Data

Dec. 20, 2002 (AT) .............................. A1910/2002

(51) Int. Cl.
*F16L 55/00* (2006.01)
*F16L 37/00* (2006.01)

(52) U.S. Cl. .............................. 285/91; 285/84; 285/86; 285/276; 285/277; 285/308; 285/316; 285/317

(58) Field of Classification Search .................. 285/81, 285/82, 84, 86, 91, 276, 277, 308, 315, 316, 285/317, 318
See application file for complete search history.

(56) References Cited

U.S. PATENT DOCUMENTS 2,552,543 A * 5/1951 Earle et al. .................. 285/277
3,110,537 A * 11/1963 Poetzsch et al. ............. 439/191
3,112,767 A * 12/1963 Cator ...................... 137/614.06
3,678,439 A * 7/1972 Vetter .......................... 439/253
3,682,506 A * 8/1972 Bruyere et al. ............. 403/299
3,817,560 A * 6/1974 Guertin ........................ 285/90
4,366,945 A * 1/1983 Blauenstein ............. 251/149.6
4,403,959 A 9/1983 Hatakeyama
4,477,253 A 10/1984 Euvrard
4,515,564 A 5/1985 Löhn
5,143,347 A * 9/1992 Lee et al. ................ 251/149.6
5,240,023 A * 8/1993 Shelef et al. ............. 137/15.09

(Continued)

FOREIGN PATENT DOCUMENTS

DE 3433877 9/1984

(Continued)

OTHER PUBLICATIONS

European Search Report (EP 1 430 851).

*Primary Examiner*—James M. Hewitt
(74) *Attorney, Agent, or Firm*—Klarquist Sparkman, LLP (57) ABSTRACT

A plug connection for fast-fit coupling of two appliances forming part of a medical handpiece system includes a first coupling fitting on one of the appliances and a second coupling fitting on the other of the appliances. The first coupling fitting has a movable locking element and the second coupling fitting has a projecting element projecting toward the first coupling fitting. The projecting element comprises an end portion of a media line or an end portion of an electrical contact and is positioned to engage a surface of an opening in the locking element to move the locking element between lock and unlock positions when the first and second coupling fittings are moved toward and away from each other.

37 Claims, 3 Drawing Sheets

U.S. PATENT DOCUMENTS 5,569,256 A    10/1996  Vaughn et al.
6,412,828 B1 *  7/2002  Lacroix et al. ............. 285/316

FOREIGN PATENT DOCUMENTS

| | | |
|---|---|---|
| DE | 197 14 276 | 4/1997 |
| EP | 0 544 274 | 11/1992 |
| EP | 0 870 477 | 3/1998 |
| EP | 0 905 432 | 3/1999 |
| FR | 2 709 658 | 2/1993 |

* cited by examiner

FAST-FIT COUPLING FOR CONNECTING APPLIANCES FORMING PART OF A MEDICAL OR SURGICAL HANDPIECE SYSTEM TO A SUPPLY HOSE

CROSS REFERENCE TO RELATED APPLICATION

The present application claims priority from pending Austrian Patent Application No. A 1910/2002, filed Dec. 20, 2002, which is incorporated herein by reference.

BACKGROUND OF THE INVENTION

1. Field

The invention concerns a fast-fit coupling for connecting appliances forming part of a medical or surgical handpiece system to a supply hose.

2. Description of Prior Art

Medical handpiece systems, consisting of a treatment instrument with a device for securing a treatment tool, a drive motor, any possibly required intermediate fittings and adapters, and a supply hose, have several interfaces which are bridged by means of couplings. Two types of couplings are currently in use for this purpose.

Various types of fast-fit couplings, e.g. plug-and-twist couplings, are used between medical appliances, e.g. a handpiece in the form of a treatment instrument and a motor. Such fast-fit couplings facilitate the rapid changing of handpieces during treatment and the removal of the handpiece for sterilization. In the main, these fast-fit couplings are in the form of spring-actuated ("non-positive") plug connections, in which the transfer of various media, such as water and air, is effected via a coupling spigot, through the perimeter of which the media exit and then continue on their path through circular channels in the opposing fitting, which then enables the handpiece to be swivelled with respect to the motor. These couplings are especially suited to treatment instruments of small diameter but with a relatively large construction length, or to applications in which a large construction length is not disadvantageous.

The connection between the supply hose and the medical appliance, e.g. a motor, is usually detachable, but not of the fast-fit type, i.e. it is mostly achieved by means of a screwed union either with or without a coupling ring, or occasionally by means of bayonet lock fittings. Previously, fast-fit couplings were not required at this point since motors could not be sterilized and the handpiece therefore only needed to be detached in order to replace a damaged hose or to service the motor. However, on account of ever increasing hygiene demands and the technical improvements which make it possible to sterilize electric motors there now exists the urgent need to create, at the interface between the supply hose and medical appliance (e.g. a motor), an ergonomically advantageous, reasonably priced coupling which is fast and easy to handle for the user and simple to manufacture. In addition, this coupling should increase the assembled length of the system as little as possible.

Conversion systems, as is known from the FR 2.709.658 B1 for example, form part of the 'state-of-the-art' environment in the sector involving interfaces between a supply hose and a medical appliance, e.g. a handpiece or motor. In this case an intermediate coupling fitting is screwed onto the coupling-side end of the supply hose, and likewise onto the hose-side end of an instrument, these two intermediate fittings can then be coupled together by means of a bayonet lock fitting.

In U.S. Pat. No. 4,477,253, a coupling is described which possesses at least one flattened surface on a circular shaped segment and which fits into the opposing fitting on the hose side. The system is locked by turning the fixing by means of a pin.

The disadvantage of both these systems is that the handpiece has to be twisted with respect to the supply hose during the coupling or detaching process, a fact which makes the coupling and uncoupling process more difficult. Often the hose is at least partially twisted instead of the motor, a process through which the hose or parts thereof can become worn and break. In addition, locking the system can only be achieved through the twisting process. This means that, if not assembled properly, the motor and hose can become separated or that the system does not function correctly. In the case of conversion systems (FR 2.709.658) additional parts are necessary, a fact which increases costs, brings along more dirt-collecting edges in its wake, extends the system and increases weight.

In U.S. Pat. No. 4,403,959, a fast-fit coupling is described which is a plug-and-twist coupling. Locking is effected by means of ball bearings. The ball bearings are held in the recesses of a sleeve via another U-shaped, rotation-symmetrical, spring-loaded sleeve, until the sleeve is pushed back when the two parts of the coupling are pushed together and the ball bearings engage in recesses on the opposing fitting. When the coupling is detached an outer sleeve is pulled back and the ball bearings are once again released.

This plug coupling corresponds to those couplings which are usually used between medical appliances, such as a handpiece and a motor, for example. However, those couplings designed in the form of a twist coupling turn out to have a disadvantage at the interface between the motor and supply hose. Since all media transfer lines have to be contained in one coupling spigot, this therefore results in increased construction length and weight and the center of gravity of the whole handpiece system changes, thus making handling more difficult for the user.

SUMMARY OF THE INVENTION

The task of the invention presented here is to create a fast-fit coupling which makes coupling and uncoupling quick and easy for the user, which requires no additional parts, does not increase weight and does not necessitate any extension of the handpiece-motor-supply-hose system. As a preference, the fast-fit coupling described in accordance with the invention could be deployed at the interface between a medical appliance, preferably a motor, and the supply hose.

According to the invention presented here the problems inherent in this task are resolved by a fast-fit coupling which comprises a plug connection including a lock element located in one of the appliances to be connected by the coupling. Further advantageous developments are described below.

In the arrangement made in accordance with the invention, the fast-fit coupling has a locking element which activates the coupling process, preferably a locking plate which is placed within one of the two appliances. In order to activate the coupling the user only has to plug together the two appliances to be coupled. The connection is shape-actuated ("positive") and is only released when the coupling sleeve is pulled back. This shape-actuated connection allows the coupling and motor to be fitted with a smooth surface, since only a relatively small pulling force is required in order to release the coupling. This means that it is possible to comply with the hygienic requirement of avoiding dirt-collecting edges. The system is cost efficient, since no additional intermediate fittings or long coupling spigots for media transfer are required and is also light and short for the same reason, a fact which has significant ergonomic advantages for operators who work with handpiece systems for several hours on a daily basis. Likewise, the avoidance of intermediate fittings results in just one break line in the form of the transfer between the coupling and the motor, which is once again a desirable characteristic from a hygienic point of view, as well as being advantageous in terms of visual appearance.

Furthermore, the invention presented here is based on the task of creating a handpiece system in which the motor to be connected to the supply hose can be coupled to and uncoupled from the supply hose quickly, easily and in a manner which does not damage the supply hose. According to the invention presented here, the problems inherent in this task are resolved by a handpiece system in which a connection between a motor and supply line is made by means of a fast-fit coupling. Further advantageous developments are described below.

In the arrangement made in accordance with an aspect of the invention, the connection is made by means of a fast-fit coupling, preferably a shape-actuated ("positive") plug connection, and the coupling process is achieved by the user merely plugging together the motor and the supply hose.

The invention is explained in the following with the aid of a preferred embodiment and in reference to the enclosed drawings:

DETAILED DESCRIPTION OF THE PREFERRED EMBODIMENTS

Figure 1:
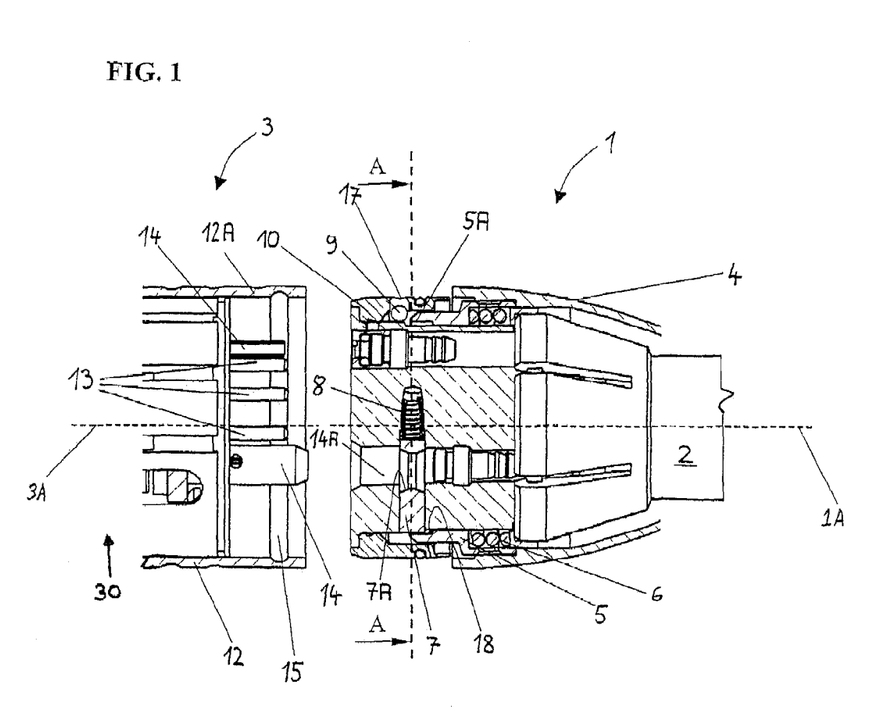
FIG. 1 shows, in accordance with the invention, a longitudinal section through the end of a motor-side supply hose and the end of the motor on the hose side in the uncoupled state.

FIG. 1 shows a hose-side coupling fitting 1 and a corresponding motor side coupling fitting 3, which motor and coupling can be sterilized, in the uncoupled state. Coupling fittings 1 and 3 have longitudinal axes 1A, 3A which are substantially aligned when the components are positioned as illustrated in FIG. 1 preparatory to push together plug-in coupling. A hose sleeve 2 is used to secure a flexible hose, via which required media, such as electricity, water and/or air, as well as a fibre optic feed from the dental unit (not depicted) or control system to the motor 30, are transported or transmitted. An annular outer sleeve 4 of hose-side coupling fitting 1 and an annular ring fitting 5 are screwed together to form a connection, and the ring fitting 5 is tensioned by a spring 6 to be urged to the left in FIG. 1. Sleeve 4 and ring fitting 5 may be moved axially of the coupling fitting as a unit between a lock position shown in FIG. 4 and an unlock position in FIG. 1. A locking element, or plate 7, is mounted within the hose-side coupling fitting 1, for movement laterally of the longitudinal axis 1A between an unlock position as seen in FIG. 1 and a lock position in FIG. 4. Plate 7 is pre-tensioned by a locking spring 8, or biasing element urging locking plate toward its unlock position as seen in FIG. 1. When in this position it engages in a step 18 located on ring fitting 5, which prevents release of tension in the spring 6 and causes the ring fitting 5 to be fixed in a displaced, or unlock, position in the direction of the hose (to the right in FIG. 1). The front or leading end 5A of the ring fitting 5 thus releases openings 17 in a bushing 10, into which several ball bearings or bearing members 9 are sunk.

Figure 4:
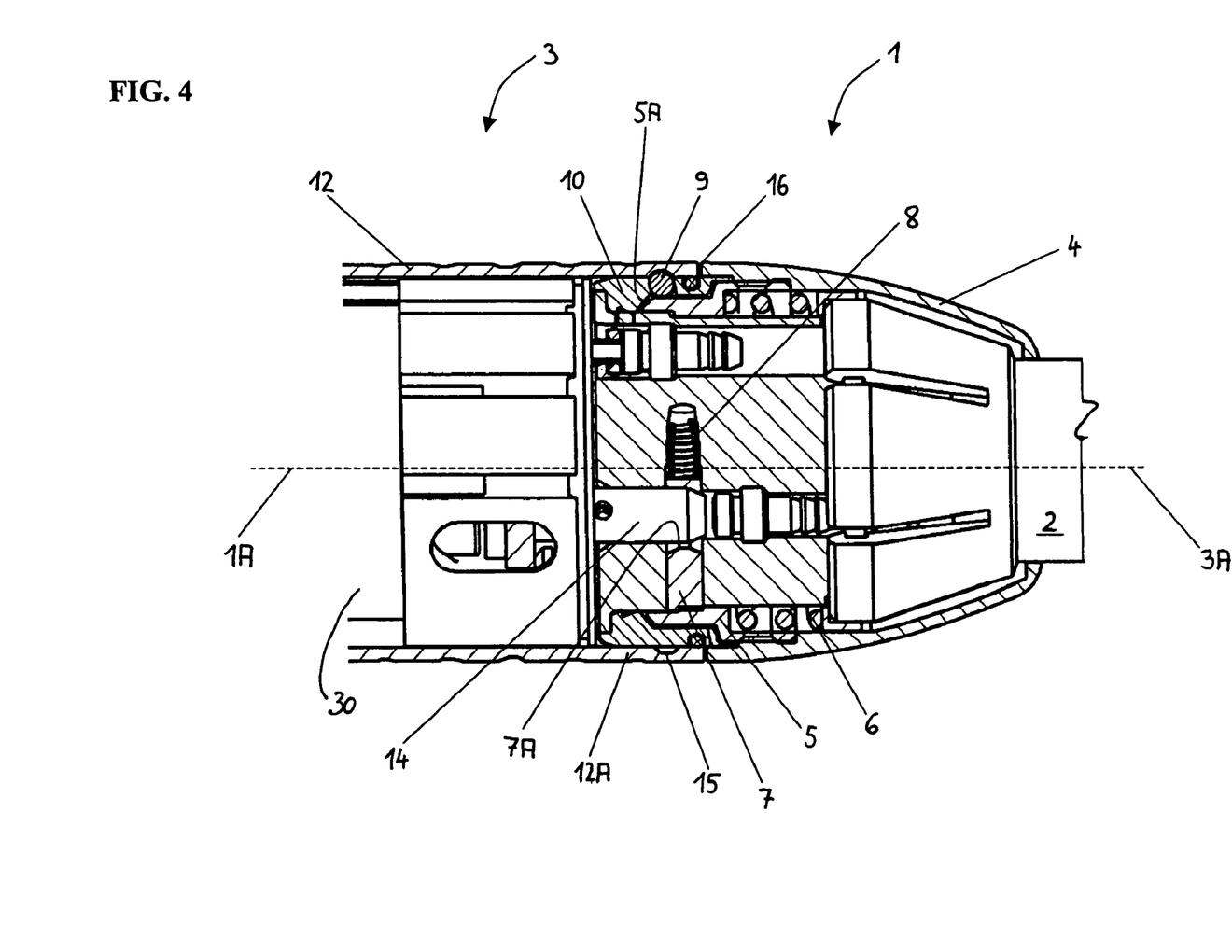
FIG. 4 shows a longitudinal section through the electric motor and the supply hose in the coupled state.

There are at least three openings 17 circumferentially arrayed about bushing 10, each of which opening is adapted to receive a ball bearing 9 for movement radially between the unlock positions shown in FIG. 1 and the lock positions in FIG. 4. Each opening 17 is tapered from a larger diameter at its radially inwardly opening end, toward a smaller radially outwardly opening end, such that a ball bearing 9 may move substantially freely radially therein with an outer portion thereof extending outwardly from bushing 10 as illustrated in FIG. 4, but preventing it from escaping from the bushing.

Figure 2:
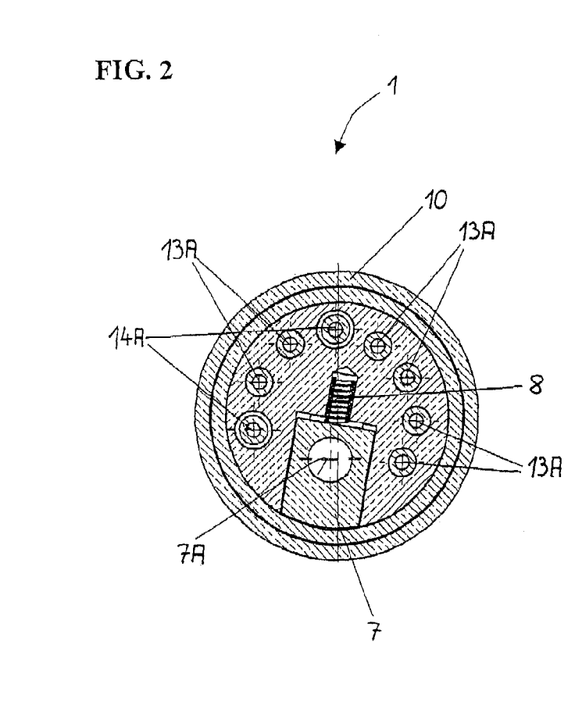
FIG. 2 shows a cross section through a coupling at the point of the locking element across line A-A in FIG. 1.

FIG. 2 represents a section along the line A-A through the hose-side coupling fitting 1. The locking element 7, as well as the locking spring 8, which presses radially outwards towards the bushing 10, is illustrated here. Moreover, receptacles 13A for electrical contacts 13 and receptacles 14A to receive media transfer lines 14 are also depicted.

Figure 3:
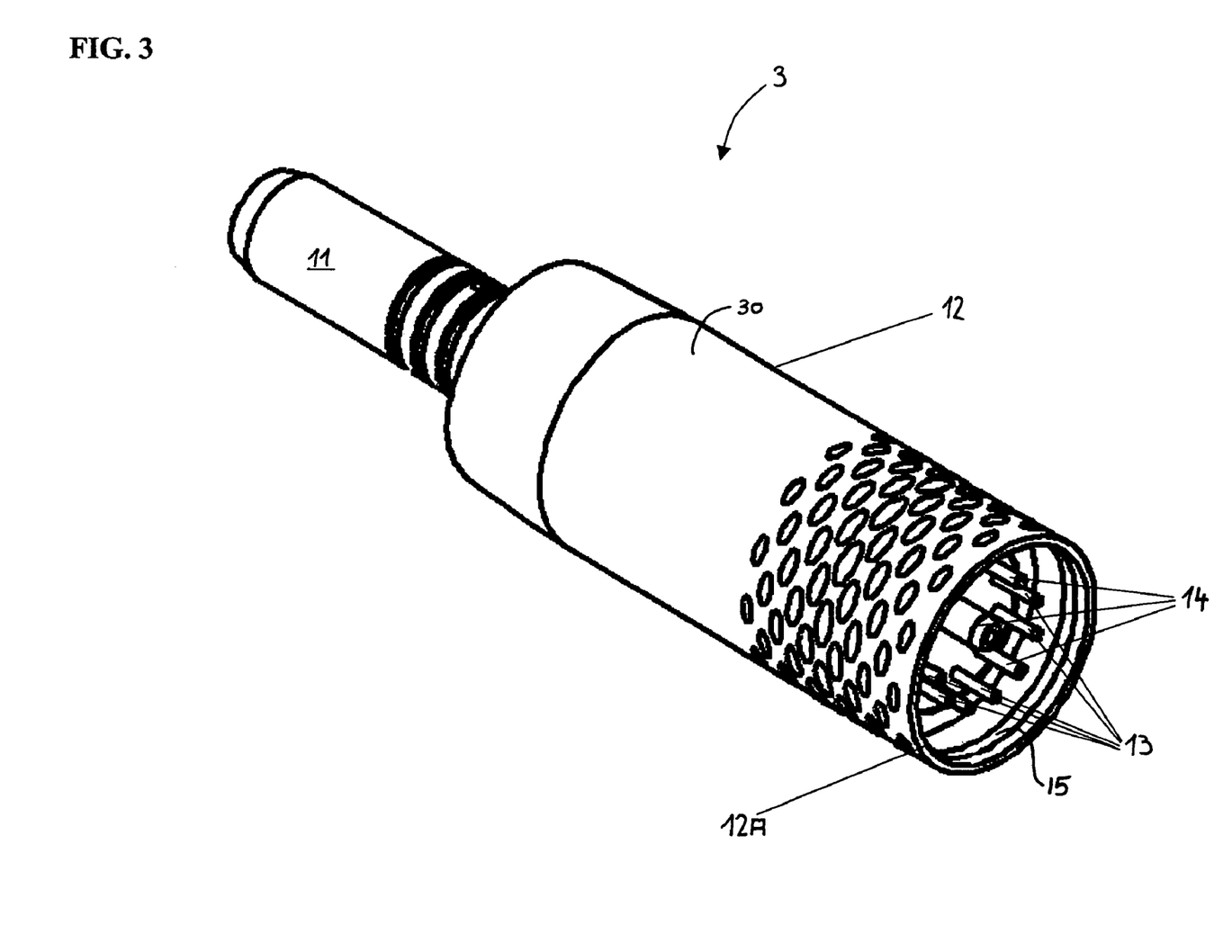
FIG. 3 shows an electric motor with the motor-side coupling half displayed in accordance with the invention.

FIG. 3 shows the motor 30 in an uncoupled state. The handpiece (not shown here) is plugged onto a coupling spigot 11 by means of a twist-type plug connection. Located in a motor sleeve 12 are, in addition to the other components necessary for the motor's function, electrical contacts 13 and media transfer lines 14 for the supply of air, e.g. a cooling air stream for the motor, and water. Furthermore, the motor sleeve 12 also includes a circumferential outer sleeve portion 12A which projects a selected distance axially from remainder portions of the coupling and possesses an annular, or circular inner groove 15, into which the ball bearings 9 engage as sealing, or securing elements in the coupled state. End portions of contacts 13 and lines 14 project axially outwardly from remainder portions of the coupling fitting with one of the lines 14 projecting at least as far as sleeve portion 12A.

FIG. 4 shows the motor side coupling 3 in the coupled state together with the hose-side coupling fitting 1. The transition from the outer sleeve 4 of the coupling fitting 1 to the motor sleeve 12 can only be detected at break line 16. When the two coupling fittings are connected, the locking element 7 is pressed laterally of the longitudinal axis 1A of the coupling, radially inwardly against its locking spring 8 into the hose-side coupling fitting 1 and held in this lock position by a media transfer line 14 extending into a bore, or opening, 7A in the locking element, (or alternatively by one of the electrical contacts 13) of the motor 30. Mating, or engaging, surfaces of a line, 13 or 14 and bore 7A are oriented such that as a line 13 or 14 enters bore 7A it urges element 7 laterally inwardly. This allows the tension in spring 6 to be released and the ring fitting 5 to move in the direction of the motor 30 to the left in FIG. 4. This in turn causes the ball bearings 9 to be pressed by ring fitting 5 outwards into the groove 15 of the sleeve 12 of the coupling fitting for motor 30. Motor side coupling fitting 3, therefore, is now coupled to the coupling fitting 1. This is a positive connection produced by selected shaped elements (ball bearings) engaging a receiving groove. This also is referred to as a shape-actuated plug connection.

In order to unlock the coupling, the outer sleeve 4 is pulled back (to the right in FIGS. 1 and 4) drawing ring fitting 5 back against the spring 6, toward its unlock position allowing the ball bearings 9 to move once again into the openings 17 of the coupling fitting 1. This causes the motor 30 to be loosened and allows the coupling fittings to be pulled axially apart and electrical contact 13 or media transfer line 14 to release the locking element 7, which is pressed outwards by the locking spring 8 and therefore blocks the ring fitting 5 once again in the retracted, or unlock, position shown in FIG. 1.

In order to guarantee positive activation of the coupling during the connection process, at least that electrical contact 13 or that media transfer line 14 which penetrates the bore 7A of the locking element 7 is of equal length to, or projects beyond the outer sleeve 12 surrounding it. Thus, the electrical contact 13 and/or the media transfer line 14 can be referred to as "projecting elements(s)."

The structure thus described allows the two coupling fittings to be assembled and joined to each other merely by pushing them toward each other in directions parallel to their longitudinal axes, with the electrical contacts and media transfer lines properly aligned with the receptacles positioned to receive them. No twisting is required, and in fact after the couplings are joined they are substantially held against rotating relative to each other. In the assembly process the lock plate, or element, is automatically shifted radially inwardly against the biasing of its tensioning spring to permit release of the ring fitting which, under the influence of spring 6, causes the ball bearings 9 to be moved forcibly into the awaiting annular groove 15 aligned therewith to positively connect the two coupling fittings to each other. Disassembly is a simple matter of merely moving the outer sleeve 4 coupled to ring fitting 5 axially of the coupling fitting against the biasing force of spring 6. This relieves the force of the ring fitting against the ball bearings, and allows ball bearings 9 to move inwardly out of the annular groove 15 to permit disassembly as shown in FIG. 1. As the coupling fittings are moved away from each other, an electrical contact 13 or media transfer line 14 moves out of bore 7A in locking element 7 allowing it to move into the stepped region of the ring fitting 5 to hold the ring fitting in its retracted position.

The invention is not restricted to the embodiment shown, but can be modified according to the construction of the motor or supply hose. Thus, for example, it is possible to use rollers instead of ball bearings or any other component of any shape which will serve the purpose. Likewise, the design of the locking element can be structured differently. Instead of the locking spring and element, for example, it is possible to use just a spring which will perform the function of both elements. The motor wiring set-up can differ according to the particular medium to be transferred, and thus the coupling fitting can also be structured differently, although this may make it necessary to deploy the locking element at another point or in another arrangement.

What is claimed is:

1. A plug connection for fast-fit coupling of two appliances forming part of a medical handpiece system, the plug connection comprising:
    a first coupling fitting capable of fitting on a first appliance and
    a second coupling fitting capable of fitting on a second appliance,
    said first coupling fitting having a movable locking element thereon and the second coupling fitting having a projecting element thereon projecting toward said first coupling fitting, the projecting element comprising an end portion of a media transfer line or an end portion of an electrical contact and being positioned to engage a surface of an opening in said locking element to move said locking element between lock and unlock positions when said first and second coupling fittings are moved toward and away from each other, respectively.

2. The plug connection of claim 1, which further comprises a biasing element urging said locking element from its lock position toward its unlock position.

3. The plug connection of claim 1, wherein said locking element and projecting element have mating surfaces which engage one another to cause the locking element to move toward its lock position when said coupling fittings are joined.

4. The plug connection of claim 1, wherein said second coupling fitting comprises a circumferential outer sleeve which projects axially outwardly a selected distance from remainder portions of said second coupling fitting and extends about an outer portion of said first coupling fitting when joined, and said projecting element projects outwardly from said remainder portions of said second coupling fitting a distance at least as great as said selected distance.

5. The plug connection of claim 1, wherein said first coupling fitting comprises a bearing member mounted for shifting between an unlock position and a lock position spaced radially from said unlock position and a ring fitting movable between an unlock position out of urging engagement with said bearing member and a lock position urging the bearing member to its lock position, and said second coupling fitting comprises a groove oriented to align with and receive a portion of said bearing member when said bearing member is in its lock position.

6. The plug connection of claim 1, wherein said first coupling fitting comprises a bearing member mounted for shifting radially between an unlock position and a lock position spaced outwardly from said unlock position and a ring fitting movable between an unlock position out of urging engagement with said bearing member and a lock position urging the bearing member to its lock position, and said second coupling fitting comprises a groove oriented to align with and receive a portion of said bearing member when said bearing member is in its lock position.

7. The plug connection of claim 6, which further comprises a spring biasing said ring fitting from its unlock toward its lock position, said locking element when in its unlock position is oriented to engage and hold said ring fitting in its unlock position, and when said locking element is moved to its lock position it releases said ring fitting to allow said ring fitting to move toward its lock position.

8. The plug connection of claim 7, wherein said ring fitting comprises a stepped portion and said locking element engages said stepped portion when in its unlock position.

9. The plug connection of claim 6, wherein an operator sleeve is mounted on said first coupling fitting, is manually shiftable longitudinally along said first coupling between first and second positions, and is operatively connected to said ring fitting to move said ring fitting from its lock position to its unlock position.

10. The plug connection of claim 1, wherein a plurality of media transfer lines and/or electrical contacts are arranged in a selected pattern projecting axially outwardly from remainder portions of said second coupling fitting, and said first coupling fitting comprises a corresponding plurality of complementary arranged receptacles into which said media transfer lines and/or electrical contacts may extend when the first and second coupling fittings are joined.

11. The plug connection of claim 10, wherein said plurality of media transfer lines and/or electrical contacts are arrayed in a semi-circular pattern between the longitudinal axis and the outer periphery of the second coupling fitting.

12. The plug connection of claim 1, wherein the locking element is operable to move between lock and unlock positions when the said first and second coupling fittings are moved axially toward and away from each other, respectively.

13. The plug connection of claim 1, wherein the one of the first coupling fitting and second coupling fitting is associated with a motor and the other of the first coupling fitting and second coupling fitting is associated with a supply conductor, and wherein, when connected, the first coupling fitting and second coupling fitting establish a connection between the motor and the supply conductor.

14. A plug connection for fast-fit coupling of two appliances forming part of a medical handpiece system, the plug connection comprising,
a first coupling fitting capable of fitting on a first appliance having a longitudinal axis, said first coupling fitting having a bearing member mounted for shifting radially between an unlock position and a lock position spaced radially from said unlock position, a ring fitting movable between an unlock position out of urging engagement with said bearing member and a lock position urging it to its lock position, a spring biasing said ring fitting toward its lock position, a locking element movable between an unlock position engaging and inhibiting movement of said ring fitting from its unlock position toward its lock position and a lock position releasing said ring fitting, and a biasing element urging said locking element from its lock position toward its unlock position, and
a second coupling fitting capable of fitting on a second appliance having a longitudinal axis, said second coupling having a groove oriented to align with and receive a portion of said bearing member when the coupling fittings are engaged and said bearing member is in its lock position, and a projecting element extending axially outwardly from remainder portions of said second coupling fitting to engage a portion of said locking element and shift the locking element toward its lock position as the first and second coupling fittings are moved axially into engagement with each other.

15. The plug connection of claim 14, wherein said locking element and projecting element have mating surfaces which engage one another to cause the locking element to move toward its lock position when said coupling fittings are joined.

16. The plug connection of claim 14, wherein said second coupling fitting comprises a circumferential outer sleeve which projects axially outwardly a selected distance from remainder portions of said second coupling fitting and extends about an outer portion of said first coupling fitting when joined, and said projecting element projects outwardly from said remainder portions of said second coupling fitting a distance at least as great as said selected distance.

17. The plug connection of claim 16, wherein said groove is formed on an inner surface of said outer sleeve and said bearing member is shifted by the ring fitting outwardly towards its lock position when the first and second coupling fittings are joined such that at least a portion of the bearing member occupies the groove.

18. The plug connection of claim 14, wherein an operator sleeve is mounted on said first coupling, is manually shiftable longitudinally along said first coupling between first and second positions, and is operatively connected to said ring fitting to move said ring fitting from its lock position to its unlock position.

19. The plug connection of claim 14, wherein a plurality of media transfer lines and/or electrical contacts are arranged in a selected pattern projecting axially outwardly from said remainder portions of said second coupling fitting, and said first coupling fitting comprises a corresponding plurality of complementary arranged receptacles into which said media transfer lines and/or electrical contacts may extend when the first and second coupling fittings are joined.

20. The plug connection of claim 14, wherein the one of the first coupling fitting and second coupling fitting is associated with a motor and the other of the first coupling fitting and second coupling fitting is associated with a supply conductor, and wherein, when connected, the first coupling fitting and second coupling fitting establish a connection between the motor and the supply conductor.

21. The plug connection of claim 14, wherein said projecting element comprises a mating surface and an end portion of a media transfer line or an end portion of an electrical contact.

22. A plug connection for fast-fit coupling of two appliances forming part of a medical handpiece system, the plug connection comprising:
a first coupling fitting capable of fitting on a first appliance and a second coupling fitting capable of fitting on a second appliance,
said first coupling fitting having a movable locking element thereon and comprising a bearing member mounted for shifting between an unlock position and a lock position spaced radially from said unlock position,
said second coupling fitting comprises a projecting element thereon projecting toward said first coupling fitting and positioned to engage and move said locking element between lock and unlock positions when said first and second coupling fittings are moved toward and away from each other, respectively.

23. The plug connection of claim 22, wherein the first coupling fitting comprises a ring fitting movable between an unlock position out of urging engagement with said bearing member and a lock position urging the bearing member to its lock position.

24. The plug connection of claim 22, wherein the second coupling fitting comprises a groove oriented to align with and receive a portion of said bearing member when said bearing member is in its lock position.

25. The plug connection of claim 22, which further comprises a biasing element urging said locking element from its lock position toward its unlock position.

26. The plug connection of claim 22, wherein said locking element and projecting element have mating surfaces which engage one another to cause the locking element to move toward its lock position when said coupling fittings are joined.

27. The plug connection of claim 22, wherein said projecting element comprises an end portion of a media transfer line and said mating surface of said locking element comprises a surface of an opening in said locking element.

28. The plug connection of claim 22, wherein said projecting element comprises an end portion of an electrical contact and said mating surface of said locking element comprises a surface of an opening in said locking element.

29. The plug connection of claim 22, wherein said second coupling fitting comprises a circumferential outer sleeve which projects axially outwardly a selected distance from remainder portions of said second coupling fitting and extends about an outer portion of said first coupling fitting when joined, and said projecting element projects outwardly from said remainder portions of said second coupling fitting a distance at least as great as said selected distance.

30. The plug connection of claim 22, wherein said bearing member is mounted for shifting radially between the unlock position and the lock position spaced outwardly from said unlock position, and a ring fitting movable between an unlock position out of urging engagement with said bearing member and a lock position urging the bearing member to its lock position, and said second coupling fitting comprises a groove oriented to align with and receive a portion of said bearing member when said bearing member is in its lock position.

31. The plug connection of claim 30, which further comprises a spring biasing said ring fining from its unlock toward its lock position, said locking element when in its unlock position is oriented to engage and hold said ring fitting in its unlock position, and when said locking element is moved to its lock position it releases said ring fitting to allow said ring fitting to move toward its lock position.

32. The plug connection of claim 31, wherein said ring fitting comprises a stepped portion and said locking element engages said stepped portion when in its unlock position.

33. The plug connection of claim 30, wherein an operator sleeve is mounted on said first coupling fitting, is manually shiftable longitudinally along said first coupling between first and second positions, and is operatively connected to said ring fitting to move said ring fitting from its lock position to its unlock position.

34. The plug connection of claim 22, wherein a plurality of media transfer lines and/or electrical contacts are arranged in a selected pattern projecting axially outwardly from remainder portions of said second coupling fitting, and said first coupling fitting comprises a corresponding plurality of complementary arranged receptacles into which said media transfer lines and/or electrical contacts may extend when the first and second coupling fittings are joined.

35. The plug connection of claim 34, wherein said plurality of media transfer lines and/or electrical contacts are arrayed in a semi-circular pattern between the longitudinal axis and the outer periphery of the second coupling fitting.

36. The plug connection of claim 22, wherein the locking element is operable to move between lock and unlock positions when the said first and second coupling fittings are moved axially toward and away from each other, respectively.

37. The plug connection of claim 22, wherein the one of the first coupling fitting and second coupling fitting is associated with a motor and the other of the first coupling fitting and second coupling fitting is associated with a supply conductor, and wherein, when connected, the first coupling fitting and second coupling fitting establish a connection between the motor and the supply conductor.

* * * * *

UNITED STATES PATENT AND TRADEMARK OFFICE
CERTIFICATE OF CORRECTION

PATENT NO.        : 7,316,424 B2
APPLICATION NO.   : 10/735317
DATED             : January 8, 2008
INVENTOR(S)       : Richard Kardeis and Wolfgang Wendtner It is certified that error appears in the above-identified patent and that said Letters Patent is hereby corrected as shown below:

<u>In the Claims:</u>
Column 9, line 17, "fining from" should read --fitting from--.

Signed and Sealed this

Nineteenth Day of August, 2008

JON W. DUDAS
*Director of the United States Patent and Trademark Office*